(12) United States Patent
Nelson et al.

(10) Patent No.: US 8,993,496 B2
(45) Date of Patent: *Mar. 31, 2015

(54) METHOD FOR IMPROVING FLUOROCARBON ELASTOMER SEAL COMPATIBILITY

(75) Inventors: Kenneth D. Nelson, Napa, CA (US); Elaine S. Yamaguchi, El Cerrito, CA (US); Kam-Sik Ng, San Lorenzo, CA (US); Paula S. Rogers, Pinole, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 262 days.

This patent is subject to a terminal disclaimer.

(21) Appl. No.: 12/798,252

(22) Filed: Mar. 31, 2010

(65) Prior Publication Data
US 2011/0245117 A1 Oct. 6, 2011

(51) Int. Cl.
| C10M 133/56 | (2006.01) |
| C10M 149/00 | (2006.01) |
| C10M 125/10 | (2006.01) |
| C10M 141/06 | (2006.01) |
| C07F 9/165 | (2006.01) |
| C10M 139/00 | (2006.01) |

(52) U.S. Cl.
CPC ............ *C07F 9/1651* (2013.01); *C10M 141/06* (2013.01); *C10M 139/00* (2013.01); C10M 2203/10 (2013.01); C10M 2203/1006 (2013.01); C10M 2203/1025 (2013.01); C10M 2205/0285 (2013.01); C10M 2207/028 (2013.01); C10M 2209/08 (2013.01); C10M 2209/082 (2013.01); C10M 2215/04 (2013.01); C10M 2215/086 (2013.01); C10M 2215/223 (2013.01); C10M 2215/28 (2013.01); C10M 2217/043 (2013.01); C10M 2217/046 (2013.01); C10M 2219/046 (2013.01); C10M 2219/089 (2013.01); C10M 2219/104 (2013.01); C10M 2223/04 (2013.01); C10M 2223/045 (2013.01); C10M 2223/06 (2013.01); C10M 2227/065 (2013.01); C10M 2227/066 (2013.01); C10M 2227/09 (2013.01); C10N 2210/04 (2013.01); C10N 2230/36 (2013.01); C10N 2240/10 (2013.01); C10N 2260/14 (2013.01)
USPC .............................. 508/165; 508/192; 508/291

(58) Field of Classification Search
USPC .......................................... 508/165, 192, 291
See application file for complete search history.

(56) References Cited

U.S. PATENT DOCUMENTS

| 3,172,892 A | 3/1965 | Le Suer et al. |
| 3,219,666 A | 11/1965 | Norman et al. |
| 3,272,746 A | 9/1966 | Le Suer et al. |
| 3,368,972 A | 2/1968 | Otto |
| 3,405,064 A | 10/1968 | Miller |
| 3,539,663 A | 11/1970 | Pietrusza et al. |
| 3,574,576 A | 4/1971 | Honnen et al. |
| 3,649,229 A | 3/1972 | Otto |
| 3,909,430 A | 9/1975 | Hotten |
| 3,968,157 A | 7/1976 | Hotten |
| 4,157,309 A | 6/1979 | Wilgus et al. |
| 4,379,064 A | 4/1983 | Cengel et al. |
| 4,615,826 A | 10/1986 | Erdman |
| 4,927,562 A | 5/1990 | Karol et al. |
| 5,114,602 A | 5/1992 | Petville et al. |
| 5,326,552 A | 7/1994 | Na et al. |
| 5,334,321 A | 8/1994 | Harrison et al. |
| 5,356,552 A * | 10/1994 | Harrison et al. ............. 508/291 |
| 5,387,351 A | 2/1995 | Kumar et al. |
| 5,405,545 A | 4/1995 | Horodysky et al. |
| 5,466,387 A | 11/1995 | Pianta et al. |
| 5,674,820 A | 10/1997 | Manka et al. |
| 5,962,380 A | 10/1999 | Tequi et al. |
| 5,972,852 A | 10/1999 | Robson |
| 6,124,247 A | 9/2000 | Cazin et al. |
| 6,172,012 B1 | 1/2001 | Kumar et al. |
| 6,372,696 B1 | 4/2002 | Tipton |
| 2004/0171501 A1 | 9/2004 | Leeuwen |
| 2006/0217271 A1* | 9/2006 | Brown et al. ................. 508/165 |
| 2007/0111908 A1 | 5/2007 | Lam et al. |
| 2007/0132274 A1 | 6/2007 | Lam et al. |
| 2007/0149418 A1 | 6/2007 | Esche et al. |
| 2007/0184992 A1 | 8/2007 | Takeuchi et al. |
| 2007/0203031 A1 | 8/2007 | Bardasz et al. |
| 2008/0139429 A1 | 6/2008 | Guinther et al. |
| 2009/0318318 A1 | 12/2009 | Mathur et al. |

FOREIGN PATENT DOCUMENTS

| EP | 0 438 849 | 11/1994 |
| EP | 0 537 386 | 11/1996 |
| EP | 0 438 847 | 11/1997 |
| EP | 0 562 062 | 1/1998 |
| EP | 0 460 309 | 5/2000 |
| EP | 1 795 582 | 6/2007 |

OTHER PUBLICATIONS

U.S. Appl. No. 12/286,377, filed Sep. 30, 2008, Yamaguchi, et al.
U.S. Appl. No. 12/653,497, filed Dec. 15, 2009, Bhalla et al.
U.S. Appl. No. 12/653,498, filed Dec. 15, 2009, Bhalla et al.
International Search Report issued in counterpart International Patent Appln. No. PCT/US2011/027349.
Singapore Search Report issued in counterpart Singapore Patent Application No. 2012006781-5 dated Feb. 14, 2014.

* cited by examiner

*Primary Examiner* — James Goloboy

(57) ABSTRACT

Disclosed is a method for improving compatibility of a fluorocarbon elastomer seal with a lubricating oil composition containing (a) a major amount of a base oil of lubricating viscosity; and (b) one or more dispersants containing one or more basic nitrogen atoms. The method involves adding to the lubricating oil composition an effective amount of one or more fluorocarbon elastomer compatibility improving agents comprising one or more oil-soluble titanium compounds.

15 Claims, No Drawings

METHOD FOR IMPROVING FLUOROCARBON ELASTOMER SEAL COMPATIBILITY

BACKGROUND OF THE INVENTION

1. Technical Field

The present invention generally relates to a method for improving fluorocarbon elastomer seal compatibility.

2. Description of the Related Art

Lubricating oil compositions used to lubricate internal combustion engines and transmissions contain a major amount of a base oil of lubricating viscosity, or a mixture of such oils, and one or more lubricating oil additives to improve the performance characteristics of the oil. For example, lubricating oil additives are used to improve detergency, to reduce engine wear, to provide stability against heat and oxidation, to reduce oil consumption, to inhibit corrosion, to act as a dispersant, and to reduce friction loss. Some additives provide multiple benefits such as, for example dispersant-viscosity modifiers.

Among the most important additives are dispersants which, as their name indicates, are used to provide engine cleanliness and to keep, for example, carbonate residues, carboxylate residues, carbonyl residues, soot, etc., in suspension. The most widely used dispersants today are products of the reaction of succinic anhydrides substituted in alpha position by an alkyl chain of polyisobutylene (PIBSA) type with a polyalkylene amine, optionally post-treated with a boron derivative, ethylene carbonate or other post-treatment reagents known in the specialized literature.

Among the polyamines used, polyalkylene-amines are preferred, such as diethylene triamine (DETA), triethylene tetramine (TETA), tetraethylene pentamine (TEPA), pentaethylene hexamine (PEHA) and heavier poly-alkylene-amines (HPA).

These polyalkylene amines react with the succinic anhydrides substituted by alkyl groups of polyisobutylene (PIBSA) type to produce, according to the molar ratio of these two reagents, mono-succinimides, bis-succinimides or mixtures of mono- and bis-succinimides Such reaction products, optionally post-treated, generally have a non-zero basic nitrogen content of the order of 5 to 50, as measured by the total base number or TBN, expressed as mg of KOH per gram of sample, which enables them to protect the metallic parts of an engine while in service from corrosion by acidic components originating from the oxidation of the lubricating oil or the fuel, while keeping the said oxidation products dispersed in the lubricating oil to prevent their agglomeration and their deposition onto metal parts.

Dispersants of mono-succinimide or bis-succinimide type are even more effective if their relative basic nitrogen content is high, i.e. in so far as the number of nitrogen atoms of the polyamine is larger than the number of succinic anhydride groups substituted by a polyisobutenyl group.

However, the higher the basic nitrogen content of these dispersants, the more they favor the attack of the fluorocarbon elastomer seals used in modern engines, because the basic nitrogen tends to react with the acidic hydrogen atoms of this type of seal, and this attack results in the formation of cracks in the elastomer surface and the loss of other physical properties sought in this type of material.

U.S. Pat. No. 6,124,247 ("the '247 patent") discloses that dispersants of mono-succinimides or bis-succinimides are even more effective if their relative basic nitrogen content is high, i.e., insofar as the number of nitrogen atoms of the polyamine is larger than the number of succinic anhydride groups substituted by a polyisobutenyl group. However, the higher the basic nitrogen content of these dispersants, the more they favor the attack of the fluoroelastomer seal used in modern engines, because the basic nitrogen tends to reach with the acidic hydrogen atoms of this type of seal, and this attack results in the formation of cracks in the elastomer surface and the loss of other physical properties sought in this type of material. The '247 patent further discloses that by using lubricating oil compositions containing a dispersant of mono-succinimide or bis-succinimide type, post-treated or not, in combination with a borated glycerol ester, one obtains a composition compatible with fluorocarbon elastomers Accordingly, it would be desirable to develop lubricating oil compositions which exhibit improved fluorocarbon elastomer seal compatibility.

SUMMARY OF THE INVENTION

In accordance with one embodiment of the present invention, there is provided a method for improving compatibility of a fluorocarbon elastomer seal with a lubricating oil composition comprising (a) a major amount of a base oil of lubricating viscosity; and (b) one or more dispersants containing one or more basic nitrogen atoms, the method comprising adding to the lubricating oil composition an effective amount of one or more fluorocarbon elastomer compatibility improving agents comprising one or more oil-soluble titanium compounds.

In accordance with a second embodiment of the present invention, there is provided a method for improving compatibility of a fluorocarbon elastomer seal with a lubricating oil composition comprising (a) a major amount of a base oil of lubricating viscosity; and (b) one or more dispersants containing one or more basic nitrogen atoms, the method comprising adding to the lubricating oil composition an effective amount of one or more fluorocarbon elastomer compatibility improving agents of the general formula of the general formula:

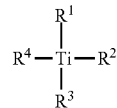

wherein $R^1$, $R^2$, $R^3$ and $R^4$ are independently a hydrocarbyloxy-containing group.

In accordance with a third embodiment of the present invention, there is provided a method for maintaining or improving compatibility of a fluorocarbon elastomer seal with a lubricating oil composition in an internal combustion engine which comprises operating the engine with a lubricating oil composition comprising (a) a major amount of a base oil of lubricating viscosity; (b) one or more dispersants containing one or more basic nitrogen atoms; and (c) an effective amount of one or more fluorocarbon elastomer compatibility improving agents comprising one or more oil-soluble titanium compounds.

The method of the present invention advantageously improves compatibility of a fluorocarbon elastomer seal with a lubricating oil composition comprising (a) a major amount of a base oil of lubricating viscosity; and (b) one or more dispersants containing one or more basic nitrogen atoms, by adding to the lubricating oil composition an effective amount of one or more fluorocarbon elastomer compatibility improving agents comprising one or more oil-soluble titanium compounds.

DETAILED DESCRIPTION OF THE PREFERRED EMBODIMENTS

The present invention is directed to a method for improving compatibility of a fluorocarbon elastomer seal with a lubricating oil composition comprising (a) a major amount of a base oil of lubricating viscosity; and (b) one or more dispersants containing one or more basic nitrogen atoms. In general, the method involves at least adding to the lubricating oil composition an effective amount of one or more fluorocarbon elastomer compatibility improving agents comprising one or more oil-soluble titanium compounds.

Generally, the one or more oil-soluble titanium compounds are represented by the general formula:

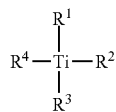

wherein $R^1$, $R^2$, $R^3$ and $R^4$ are independently a hydrocarbyloxy-containing group. Examples of such hydrocarbyloxy-containing groups include, but are not limited to, a $C_1$ to $C_{20}$ alkoxy group, $C_6$ to $C_{20}$ aryloxy group, $C_7$ to $C_{20}$ alkylaryloxy group, $C_7$ to $C_{20}$ arylalkyloxy group, $C_6$ to $C_{20}$ cycloalkyloxy group, $C_7$ to $C_{20}$ cycloalkylalkyloxy group, $C_7$ to $C_{20}$ alkylcycloalkyloxy group and the like and mixtures thereof. In one embodiment, each $R^1$, $R^2$, $R^3$ and $R^4$ is independently a $C_1$ to $C_{20}$ alkoxy group, $C_6$ to $C_{20}$ aryloxy group, and a $C_1$ to $C_6$ acyloxy group. In another embodiment, each $R^1$, $R^2$, $R^3$ and $R^4$ is independently a $C_1$ to $C_{20}$ alkoxy group or $C_3$ to $C_8$ alkoxy group. In another embodiment, at least two of $R^1$, $R^2$, $R^3$ and $R^4$ are the same $C_1$ to $C_{20}$ alkoxy group or $C_3$ to $C_8$ alkoxy group. In another embodiment, at least three of $R^1$, $R^2$, $R^3$ and $R^4$ are the same $C_1$ to $C_{20}$ alkoxy group or $C_3$ to $C_8$ alkoxy group. In one preferred embodiment, each of $R^1$, $R^2$, $R^3$ and $R^4$ are the same $C_1$ to $C_{20}$ alkoxy group or $C_3$ to $C_8$ alkoxy group.

Representative examples of alkoxy groups for use herein include, by way of example, an alkyl group as defined herein attached via oxygen linkage to the rest of the molecule, i.e., of the general Formula —$OR^5$, wherein $R^5$ is an alkyl, cycloalkyl, cycloalkylalkyl, cycloalkenyl, aryl or an arylalkyl as defined herein, e.g., —$OCH_3$, —$OC_2H_5$, or —$OC_6H_5$, and the like.

Representative examples of alkyl groups for use herein include, by way of example, a straight or branched alkyl chain radical containing carbon and hydrogen atoms of from 1 to about 20 carbon atoms and preferably from 1 to about 8 carbon atoms with or without unsaturation, to the rest of the molecule, e.g., methyl, ethyl, n-propyl, isopropyl, n-butyl, n-pentyl, etc., and the like.

Representative examples of cycloalkyl groups for use herein include, by way of example, a substituted or unsubstituted non-aromatic mono or multicyclic ring system of about 6 to about 20 carbon atoms such as, for example, cyclopropyl, cyclobutyl, cyclopentyl, cyclohexyl, bridged cyclic groups or sprirobicyclic groups, e.g., spiro-(4,4)-non-2-yl and the like, optionally containing one or more heteroatoms, e.g., O and N, and the like.

Representative examples of cycloalkylalkyl groups for use herein include, by way of example, a substituted or unsubstituted cyclic ring-containing radical containing from about 7 to about 20 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 6 to about 20 carbon atoms such as, for example, phenyl, naphthyl, tetrahydronapthyl, indenyl, biphenyl and the like, optionally containing one or more heteroatoms, e.g., O and N, and the like.

Representative examples of arylalkyl groups for use herein include, by way of example, a substituted or unsubstituted aryl group containing from about 7 to about 20 carbon atoms directly attached to the alkyl group which is then attached to the main structure of the monomer at any carbon from the alkyl group that results in the creation of a stable structure such as, e.g., —$CH_2C_6H_5$, —$C_2H_5C_6H_5$ and the like, wherein the aryl group can optionally contain one or more heteroatoms, e.g., O and N, and the like.

In one embodiment, representative examples of suitable oil-soluble titanium compounds represented by the structure of Formula I includes titanium (IV) alkoxides such as titanium methoxide, titanium ethoxide, titanium propoxide, titanium isopropoxide, titanium butoxide, titanium 2-ethylhexoxide, titanium isobutoxide, titanium 4-methyl-2-pentoxide, titanium hexoxide, titanium pentoxide, titanium isopentoxide, titanium triethanolaminato-isopropoxide and the like and mixtures thereof.

The oil-soluble titanium compounds disclosed herein are commercially available or can be readily prepared by appropriate synthesis techniques which will be apparent to the person skilled in the art. In addition, they may exist at room temperature as a solid or a liquid, depending on the particular compound. Alternatively, they may also be provided in a solution form in an appropriate inert solvent.

Generally, the amount of the one or more fluorocarbon elastomer compatibility improving agents, i.e., the one or more oil-soluble titanium compounds, in the lubricating oil composition will vary from about 0.01 to about 5 wt. %, based on the total weight of the lubricating oil composition. In another embodiment, the amount of the one or more fluorocarbon elastomer compatibility improving agents will vary from about 0.1 to about 2.5 wt. %, based on the total weight of the lubricating oil composition.

The lubricating oil compositions can be prepared by admixing, by conventional techniques, an appropriate amount of one or more fluorocarbon elastomer compatibility improving agents with (a) a major amount of a base oil of lubricating viscosity; and (b) one or more dispersants containing one or more basic nitrogen atoms. The selection of the particular base oil depends on the contemplated application of the lubricant and the presence of other additives. The base oil of lubricating viscosity for use in the lubricating oil compositions disclosed herein is typically present in a major amount, e.g., an amount of greater than 50 wt. %, preferably greater than about 70 wt. %, more preferably from about 80 to about 99.5 wt. % and most preferably from about 85 to about 98 wt. %, based on the total weight of the composition. The expression "base oil" as used herein shall be understood to mean a base stock or blend of base stocks which is a lubricant component that is produced by a single manufacturer to the same specifications (independent of feed source or manufacturer's location); that meets the same manufacturer's specification; and that is identified by a unique formula, product identification number, or both.

The base oil for use herein can be any presently known or later-discovered base oil of lubricating viscosity used in formulating lubricating oil compositions for any and all such applications, e.g., engine oils, marine cylinder oils, functional fluids such as hydraulic oils, gear oils, transmission fluids, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fischer-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500, etc.) or mono- and polycarboxylic esters thereof such as, for example, the acetic esters, mixed $C_3$-$C_8$ fatty acid esters, or the $C_{13}$ oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl)silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The lubricating oil compositions also contain one or more dispersants containing one or more basic nitrogen atoms. The basic nitrogen compound for use herein must contain basic nitrogen as measured, for example, by ASTM D664 test or D2896. The basic nitrogen compounds are selected from the group consisting of succinimides, polysuccinimides, carboxylic acid amides, hydrocarbyl monoamines, hydrocarbon polyamines, Mannich bases, phosphoramides, thiophosphoramides, phosphonamides, dispersant viscosity index improvers, and mixtures thereof. These basic nitrogen-containing compounds are described below (keeping in mind the reservation that each must have at least one basic nitrogen). Any of the nitrogen-containing compositions may be post-treated with, e.g., boron or ethylene carbonate, using procedures well known in the art so long as the compositions continue to contain basic nitrogen.

The mono and polysuccinimides that can be used to prepare the dispersants described herein are disclosed in numerous references and are well known in the art. Certain fundamental types of succinimides and the related materials encompassed by the term of art "succinimide" are taught in U.S. Pat. Nos. 3,172,892; 3,219,666; and 3,272,746, the disclosures of which are incorporated by reference herein. The term "succinimide" is understood in the art to include many of the amide, imide, and amidine species which may also be formed. The predominant product however is a succinimide and this term has been generally accepted as meaning the product of a reaction of an alkenyl substituted succinic acid or anhydride with a nitrogen-containing compound. Preferred succinimides, because of their commercial availability, are those succinimides prepared from a hydrocarbyl succinic anhydride, wherein the hydrocarbyl group contains from about 24 to about 350 carbon atoms, and an ethylene amine, said ethylene amines being especially characterized by ethylene diamine, diethylene triamine, triethylene tetramine, and tetraethylene pentamine. In one embodiment, the succinimides are prepared from a polyisobutenyl succinic anhydride of about 70 to about 128 carbon atoms and tetraethylene pentamine or triethylene tetramine or mixtures thereof.

Also included within the term "succinimide" are the cooligomers of a hydrocarbyl succinic acid or anhydride and a poly secondary amine containing at least one tertiary amino nitrogen in addition to two or more secondary amino groups. Ordinarily this composition has between about 1,500 and about 50,000 average molecular weight.

Carboxylic acid amide compositions are also suitable starting materials for preparing the dispersants employed in this invention. Examples of such compounds are those disclosed in U.S. Pat. No. 3,405,064, the disclosure of which is hereby incorporated by reference. These dispersants are ordinarily prepared by reacting a carboxylic acid or anhydride or ester thereof, having at least about 12 to about 350 aliphatic carbon atoms in the principal aliphatic chain and, if desired, having sufficient pendant aliphatic groups to render the molecule oil soluble with an amine or a hydrocarbyl polyamine, such as an ethylene amine, to give a mono or polycarboxylic acid amide. Preferred are those amides prepared from (1) a carboxylic acid of the formula R'COOH, where R' is $C_{12}$ to $C_{20}$ alkyl or a mixture of this acid with a polyisobutenyl carboxylic acid in which the polyisobutenyl group contains from about 72 to about 128 carbon atoms and (2) an ethylene amine, especially triethylene tetramine or tetraethylene pentamine or mixtures thereof.

Another class of compounds which are useful in this invention is hydrocarbyl monoamines and hydrocarbyl polyamines, preferably of the type disclosed in U.S. Pat. No. 3,574,576, the disclosure of which is incorporated by reference herein. The hydrocarbyl group, which is preferably alkyl, or olefinic having one or two sites of unsaturation, usually contains from about 9 to about 350, preferably from about 20 to about 200 carbon atoms. In one embodiment, a hydrocarbyl polyamine can be one derived, e.g., by reacting polyisobutenyl chloride and a polyalkylene polyamine, such as an ethylene amine, e.g., ethylene diamine, diethylene triamine, tetraethylene pentamine, 2-aminoethylpiperazine, 1,3-propylene diamine, 1,2-propylenediamine, and the like.

Another class of compounds useful for supplying basic nitrogen is the Mannich base compositions. These compositions are prepared from a phenol or $C_9$ to $C_{200}$ alkylphenol, an aldehyde, such as formaldehyde or formaldehyde precursor such as paraformaldehyde, and an amine compound. The amine may be a mono or polyamine and typical compositions are prepared from an alkylamine, such as methylamine or an ethylene amine, such as, diethylene triamine, or tetraethylene pentamine, and the like. The phenolic material may be sulfurized and preferably is dodecylphenol or a $C_{80}$ to $C_{100}$ alkylphenol. Typical Mannich bases which can be used in this invention are disclosed in U.S. Pat. Nos. 3,368,972; 3,539,663; 3,649,229; and 4,157,309, the disclosures of which are incorporated by reference herein. U.S. Pat. No. 3,539,663 discloses Mannich bases prepared by reacting an alkylphenol having at least 50 carbon atoms, preferably 50 to 200 carbon atoms with formaldehyde and an alkylene polyamine $HN(ANH)_nH$ where A is a saturated divalent alkyl hydrocarbon of 2 to 6 carbon atoms and n is 1-10 and where the condensation product of said alkylene polyamine may be further reacted with urea or thiourea. The utility of these Mannich bases as starting materials for preparing lubricating oil additives can often be significantly improved by treating the Mannich base using conventional techniques to introduce boron into the composition.

Another class of composition useful for preparing the dispersants employed in this invention is the phosphoramides and phosphonamides, such as those disclosed in U.S. Pat. Nos. 3,909,430 and 3,968,157, the disclosures of which are incorporated by reference herein. These compositions may be prepared by forming a phosphorus compound having at least one P—N bond. They can be prepared, for example, by reacting phosphorus oxychloride with a hydrocarbyl diol in the presence of a monoamine or by reacting phosphorus oxychloride with a difunctional secondary amine and a mono-functional amine. Thiophosphoramides can be prepared by reacting an unsaturated hydrocarbon compound containing from about 2 to about 450 or more carbon atoms, such as polyethylene, polyisobutylene, polypropylene, ethylene, 1-hexene, 1,3-hexadiene, isobutylene, 4-methyl-1-pentene, and the like, with phosphorus pentasulfide and a nitrogen-containing compound as defined above, particularly an alkylamine, alkyldiamine, alkylpolyamine, or an alkyleneamine, such as ethylene diamine, diethylenetriamine, triethylenetetramine, tetraethylenepentamine, and the like.

Another class of nitrogen-containing compositions useful in preparing the dispersants employed in this invention includes the so-called dispersant viscosity index improvers (VI improvers). These VI improvers are commonly prepared by functionalizing a hydrocarbon polymer, especially a polymer derived from ethylene and/or propylene, optionally containing additional units derived from one or more co-monomers such as alicyclic or aliphatic olefins or diolefins. The functionalization may be carried out by a variety of processes which introduce a reactive site or sites which usually has at least one oxygen atom on the polymer. The polymer is then contacted with a nitrogen-containing source to introduce nitrogen-containing functional groups on the polymer backbone. Commonly used nitrogen sources include any basic nitrogen compound especially those nitrogen-containing compounds and compositions described herein. Preferred nitrogen sources are alkylene amines, such as ethylene amines, alkyl amines, and Mannich bases.

In one preferred embodiment, the basic nitrogen compounds for use in making the dispersants are succinimides, carboxylic acid amides, and Mannich bases. In another preferred embodiment, the basic nitrogen compounds for use in making the dispersants are succinimides having an average molecular weight of about 1000 or about 1300 or about 2300 and mixtures thereof. Such succinimides can be post treated with boron or ethylene carbonate as known in the art.

Generally, the amount of the one or more dispersants in the lubricating oil composition will vary from about 0.05 to about 15 wt. %, based on the total weight of the lubricating oil composition. In another embodiment, the amount of the one or more dispersants will vary from about 0.1 to about 9 wt. %, based on the total weight of the lubricating oil composition.

The lubricating oil compositions may also contain other conventional lubricating oil additives for imparting auxiliary functions to give a finished lubricating oil composition in which these additives are dispersed or dissolved. For example, the lubricating oil compositions can be blended with antioxidants, detergents such as metal detergents, rust inhibitors, dehazing agents, demulsifying agents, metal deactivating agents, friction modifiers, antiwear agents, pour point depressants, antifoaming agents, co-solvents, package compatibilisers, corrosion-inhibitors, dyes, extreme pressure agents and the like and mixtures thereof. A variety of the additives are known and commercially available. These additives, or their analogous compounds, can be employed for the preparation of the lubricating oil compositions of the invention by the usual blending procedures.

Examples of antioxidants include, but are not limited to, aminic types, e.g., diphenylamine, phenyl-alpha-napthylamine, N,N-di(alkylphenyl)amines; and alkylated phenylene-diamines; phenolics such as, for example, BHT, sterically hindered alkyl phenols such as 2,6-di-tert-butylphenol, 2,6-di-tert-butyl-p-cresol and 2,6-di-tert-butyl-4-(2-octyl-3-propanoic)phenol; and mixtures thereof.

Representative examples of metal detergents include sulphonates, alkylphenates, sulfurized alkyl phenates, carboxylates, salicylates, phosphonates, and phosphinates. Commercial products are generally referred to as neutral or overbased. Overbased metal detergents are generally produced by carbonating a mixture of hydrocarbons, detergent acid, for example: sulfonic acid, alkylphenol, carboxylate etc., metal oxide or hydroxides (for example calcium oxide or calcium hydroxide) and promoters such as xylene, methanol and water. For example, for preparing an overbased calcium sulfonate, in carbonation, the calcium oxide or hydroxide reacts with the gaseous carbon dioxide to form calcium carbonate. The sulfonic acid is neutralized with an excess of CaO or $Ca(OH)_2$, to form the sulfonate.

Metal-containing or ash-forming detergents function as both detergents to reduce or remove deposits and as acid neutralizers or rust inhibitors, thereby reducing wear and corrosion and extending engine life. Detergents generally comprise a polar head with a long hydrophobic tail. The polar head comprises a metal salt of an acidic organic compound. The salts may contain a substantially stoichiometric amount of the metal in which case they are usually described as normal or neutral salts, and would typically have a total base number or TBN (as can be measured by ASTM D2896) of from 0 to about 80. A large amount of a metal base may be incorporated by reacting excess metal compound (e.g., an oxide or hydroxide) with an acidic gas (e.g., carbon dioxide). The resulting overbased detergent comprises neutralized detergent as the outer layer of a metal base (e.g., carbonate) micelle. Such overbased detergents may have a TBN of about 150 or greater, and typically will have a TBN of from about 250 to about 450 or more.

Detergents that may be used include oil-soluble neutral and overbased sulfonates, phenates, sulfurized phenates, thiophosphonates, salicylates, and naphthenates and other oil-soluble carboxylates of a metal, particularly the alkali or alkaline earth metals, e.g., barium; sodium, potassium, lithium, calcium, and magnesium. The most commonly used metals are calcium and magnesium, which may both be present in detergents used in a lubricant, and mixtures of calcium and/or magnesium with sodium. Particularly convenient metal detergents are neutral and overbased calcium sulfonates having TBN of from about 20 to about 450, neutral and overbased calcium phenates and sulfurized phenates having TBN of from about 50 to about 450 and neutral and overbased magnesium or calcium salicylates having a TBN of from about 20 to about 450. Combinations of detergents, whether overbased or neutral or both, may be used.

In one embodiment, the detergent can be one or more alkali or alkaline earth metal salts of an alkyl-substituted hydroxyaromatic carboxylic acid. Suitable hydroxyaromatic compounds include mononuclear monohydroxy and polyhydroxy aromatic hydrocarbons having 1 to 4, and preferably 1 to 3, hydroxyl groups. Suitable hydroxyaromatic compounds include phenol, catechol, resorcinol, hydroquinone, pyrogallol, cresol, and the like. The preferred hydroxyaromatic compound is phenol.

The alkyl substituted moiety of the alkali or alkaline earth metal salt of an alkyl-substituted hydroxyaromatic carboxylic acid is derived from an alpha olefin having from about 10 to about 80 carbon atoms. The olefins employed may be linear, isomerized linear, branched or partially branched linear. The olefin may be a mixture of linear olefins, a mixture of isomerized linear olefins, a mixture of branched olefins, a mixture of partially branched linear or a mixture of any of the foregoing.

In one embodiment, the mixture of linear olefins that may be used is a mixture of normal alpha olefins selected from olefins having from about 12 to about 30 carbon atoms per molecule. In one embodiment, the normal alpha olefins are isomerized using at least one of a solid or liquid catalyst.

In another embodiment, the olefins are a branched olefinic propylene oligomer or mixture thereof having from about 20 to about 80 carbon atoms, i.e., branched chain olefins derived from the polymerization of propylene. The olefins may also be substituted with other functional groups, such as hydroxy groups, carboxylic acid groups, heteroatoms, and the like. In one embodiment, the branched olefinic propylene oligomer or mixtures thereof have from about 20 to about 60 carbon atoms. In one embodiment, the branched olefinic propylene oligomer or mixtures thereof have from about 20 to about 40 carbon atoms.

In one embodiment, at least about 75 mole % (e.g., at least about 80 mole %, at least about 85 mole %, at least about 90 mole %, at least about 95 mole %, or at least about 99 mole %) of the alkyl groups contained within the alkali or alkaline earth metal salt of an alkyl-substituted hydroxyaromatic carboxylic acid such as the alkyl groups of an alkaline earth metal salt of an alkyl-substituted hydroxybenzoic acid detergent are a $C_{20}$ or higher. In another embodiment, the alkali or alkaline earth metal salt of an alkyl-substituted hydroxyaromatic carboxylic acid is an alkali or alkaline earth metal salt of an alkyl-substituted hydroxybenzoic acid that is derived from an alkyl-substituted hydroxybenzoic acid in which the alkyl groups are the residue of normal alpha-olefins containing at least 75 mole % $C_{20}$ or higher normal alpha-olefins.

In another embodiment, at least about 50 mole % (e.g., at least about 60 mole %, at least about 70 mole %, at least about 80 mole %, at least about 85 mole %, at least about 90 mole %, at least about 95 mole %, or at least about 99 mole %) of the alkyl groups contained within the alkali or alkaline earth metal salt of an alkyl-substituted hydroxyaromatic carboxylic acid such as the alkyl groups of an alkali or alkaline earth metal salt of an alkyl-substituted hydroxybenzoic acid are about $C_{14}$ to about $C_{18}$.

The resulting alkali or alkaline earth metal salt of an alkyl-substituted hydroxyaromatic carboxylic acid will be a mixture of ortho and para isomers. In one embodiment, the product will contain about 1 to 99% ortho isomer and 99 to 1% para isomer. In another embodiment, the product will contain about 5 to 70% ortho and 95 to 30% para isomer.

The alkali or alkaline earth metal salts of an alkyl-substituted hydroxyaromatic carboxylic acid can be neutral or overbased. Generally, an overbased alkali or alkaline earth metal salt of an alkyl-substituted hydroxyaromatic carboxylic acid is one in which the BN of the alkali or alkaline earth metal salts of an alkyl-substituted hydroxyaromatic carboxylic acid has been increased by a process such as the addition of a base source (e.g., lime) and an acidic overbasing compound (e.g., carbon dioxide).

Overbased salts may be low overbased, e.g., an overbased salt having a BN below about 100. In one embodiment, the BN of a low overbased salt may be from about 5 to about 50. In another embodiment, the BN of a low overbased salt may be from about 10 to about 30. In yet another embodiment, the BN of a low overbased salt may be from about 15 to about 20.

Overbased detergents may be medium overbased, e.g., an overbased salt having a BN from about 100 to about 250. In one embodiment, the BN of a medium overbased salt may be from about 100 to about 200. In another embodiment, the BN of a medium overbased salt may be from about 125 to about 175.

Overbased detergents may be high overbased, e.g., an overbased salt having a BN above about 250. In one embodiment, the BN of a high overbased salt may be from about 250 to about 450.

Sulfonates may be prepared from sulfonic acids which are typically obtained by the sulfonation of alkyl substituted aromatic hydrocarbons such as those obtained from the fractionation of petroleum or by the alkylation of aromatic hydrocarbons. Examples included those obtained by alkylating benzene, toluene, xylene, naphthalene, diphenyl or their halogen derivatives. The alkylation may be carried out in the presence of a catalyst with alkylating agents having from about 3 to more than 70 carbon atoms. The alkaryl sulfonates usually contain from about 9 to about 80 or more carbon atoms, preferably from about 16 to about 60 carbon atoms per alkyl substituted aromatic moiety.

The oil soluble sulfonates or alkaryl sulfonic acids may be neutralized with oxides, hydroxides, alkoxides, carbonates, carboxylate, sulfides, hydrosulfides, nitrates, borates and ethers of the metal. The amount of metal compound is chosen having regard to the desired TBN of the final product but typically ranges from about 100 to about 220 wt. % (preferably at least about 125 wt. %) of that stoichiometrically required.

Metal salts of phenols and sulfurized phenols are prepared by reaction with an appropriate metal compound such as an oxide or hydroxide and neutral or overbased products may be obtained by methods well known in the art. Sulfurized phenols may be prepared by reacting a phenol with sulfur or a sulfur containing compound such as hydrogen sulfide, sulfur monohalide or sulfur dihalide, to form products which are generally mixtures of compounds in which 2 or more phenols are bridged by sulfur containing bridges.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof.

Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$, fatty acid ester and a nitrogen-containing compound selected from the group consisting of ammonia, and an alkanolamine and the like and mixtures thereof.

Examples of antiwear agents include, but are not limited to, zinc dialkyldithiophosphates and zinc diaryldithiophosphates, e.g., those described in an article by Born et al. entitled "Relationship between Chemical Structure and Effectiveness of Some Metallic Dialkyl- and Diaryl-dithiophosphates in Different Lubricated Mechanisms", appearing in Lubrication Science 4-2 January 1992, see for example pages 97-100; aryl phosphates and phosphites, sulfur-containing esters, phosphosulfur compounds, metal or ash-free dithiocarbamates, xanthates, alkyl sulfides and the like and mixtures thereof.

Examples of antifoaming agents include, but are not limited to, polymers of alkyl methacrylate; polymers of dimethylsilicone and the like and mixtures thereof.

Each of the foregoing additives, when used, is used at a functionally effective amount to impart the desired properties to the lubricant. Thus, for example, if an additive is a friction modifier, a functionally effective amount of this friction modifier would be an amount sufficient to impart the desired friction modifying characteristics to the lubricant. Generally, the concentration of each of these additives, when used, ranges from about 0.001% to about 20% by weight, based on the total weight of the lubricating oil composition. In one embodiment, the concentration of each of these additives ranges from about 0.01% to about 10% by weight, based on the total weight of the lubricating oil composition.

The final application of the lubricating oil compositions of this invention may be, for example, in marine cylinder lubricants in crosshead diesel engines, crankcase lubricants in an internal combustion engine or railroad engines and the like. Whether the lubricating oil composition is fluid or solid will ordinarily depend on whether a thickening agent is present. Typical thickening agents include polyurea acetates, lithium stearate and the like.

In another embodiment of the invention, the one or more fluorocarbon elastomer compatibility improving agents may be provided as an additive package or concentrate in which the one or more fluorocarbon elastomer compatibility improving agents are incorporated into a substantially inert, normally liquid organic diluent such as, for example, mineral oil, naphtha, benzene, toluene or xylene to form an additive concentrate. These concentrates usually contain from about 20% to about 80% by weight of such diluent. Typically a neutral oil having a viscosity of about 4 to about 8.5 cSt at 100° C. and preferably about 4 to about 6 cSt at 100° C. will be used as the diluent, though synthetic oils, as well as other organic liquids which are compatible with the additives and finished lubricating oil can also be used. The additive package will also typically contain one or more of the various other additives, referred to above, in the desired amounts and ratios to facilitate direct combination with the requisite amount of base oil.

The following non-limiting examples are illustrative of the present invention.

Comparative Example A

A baseline lubricating oil composition was prepared by blending together the following components to obtain a SAE 15W-40 viscosity grade formulation:

(a) 4 wt. % of a borated bissuccinimide prepared from a polyisobutenyl (PIB) succinic anhydride (the PIB having an average molecular weight of 1300) with a heavy polyamine;

(b) 2 wt. % of an ethylene carbonate post-treated bissuccinimide prepared from a PIB succinic anhydride (the PIB having an average molecular weight of 2300) with a heavy polyamine;

(c) 3 wt. % of a polysuccinimide dispersant derived from PIBSA, N-phenyl phenylenediamine and a polyetherdiamine having an average molecular weight of 900 to 1000;

(d) sulfurized calcium phenate detergent;

(e) zinc dialkyldithiophosphate;

(f) borated sulfonate detergent;

(g) magnesium sulfonate detergent;

(h) calcium sulfonate detergent;

(i) a molybdenum succinimide complex;

(j) one or more oxidation inhibitors;

(k) foam inhibitor;

(l) viscosity index improver; and (m) the balance being a mixture of Group II base oils.

Example 1

A lubricating oil composition was prepared by adding 1 weight % of titanium (IV) isopropoxide (available from DuPont as Tyzor® TPT) to the baseline lubricating oil composition of Comparative Example A.

Evaluation of Fluorocarbon Elastomer Seal Compatibility

The lubricating oil compositions of Comparative Example A and Example 1 were tested for compatibility with fluorocarbon elastomer seals in a Volkswagen (VW) bench test (PV 3344) by suspending a fluorocarbon test piece (AK 6) in an oil-based solution heated to 150° C. for 168 hours. The variation in the percent volume change, points hardness change (PH), the percent tensile strength change (TS) and the percent elongation change (EL) of each sample was measured. The results are summarized in Table 1.

TABLE 1

|  | Example 1 | Comp. Ex. A | Passing Limit |
|---|---|---|---|
| Vol. Change (%) | 0.11 | 0.29 | ≤0.5 |
| PH Change | 2 | 4 | ≤5 |
| TS Change (%) | −42.4 | −54.3 | ≥−50 |
| EL Change (%) | −30.0 | −36.7 | ≥−55 |

The results demonstrate that the lubricating oil composition of Example 1 provided improved fluorocarbon elastomer seal compatibility in all categories and passed each of the seal tests. These results indicate that by adding titanium (IV) isopropoxide to a lubricating oil composition containing one or more dispersants containing one or more basic nitrogen atoms, the fluorocarbon elastomer seal is protected from other components in the baseline lubricating oil composition (Comp. Ex. A).

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A method for improving compatibility of a fluorocarbon elastomer seal with a lubricating oil composition having one or more dispersants containing one or more basic nitrogen atoms in an internal combustion engine containing fluorocarbon elastomer seals, the method comprising operating an internal combustion engine containing fluorocarbon elastomer seals with a lubricating oil composition comprising a) a major amount of a base oil of lubricating viscosity; (b) a dispersant mixture containing (i) a borated post-treated bis-succinimide, (ii an ethylene carbonate post-treated bissuccinimide and (iii) a polysuccinimide; and (c) an effective amount of one or more fluorocarbon elastomer compatibility improving agents comprising one or more oil-soluble titanium compounds, wherein the internal combustion engine is in need of improved fluorocarbon elastomer seal compatibility with the lubricating oil composition.

2. The method of claim 1, wherein the base oil of lubricating viscosity is selected from the group consisting of a Group I base oil, Group II base oil, Group III base oil, Group IV base oil, Group V base oil, and mixtures thereof.

3. The method of claim 1, wherein the amount of the dispersant mixture in the lubricating oil composition is from about 0.05 to about 15 wt. % based on the total weight of the lubricating oil composition.

4. The method of claim 1, wherein the one or more oil-soluble titanium compounds are selected from the group consisting of titanium (IV) isopropoxide, titanium (IV) n-propoxide, titanium (IV) 2-ethylhexoxide and mixtures thereof.

5. The method of claim 1, wherein the amount of the one or more fluorocarbon elastomer compatibility improving agents is about 0.01 to about 5 wt. %, based on the total weight of the lubricating oil composition.

6. The method of claim 1, wherein the amount of the one or more fluorocarbon elastomer compatibility improving agents is about 0.1 to about 2.5 wt. %, based on the total weight of the lubricating oil composition.

7. The method of claim 1, wherein the one or more fluorocarbon elastomer compatibility improving agents further comprise a diluent oil to form an additive concentrate.

8. The method of claim 1, wherein the lubricating oil composition is a crankcase lubricating oil composition for an internal combustion engine.

9. The method of claim 1, wherein the lubricating oil composition comprises:
about 0.05 to about 15 wt. % of the dispersant mixture; and
about 0.01 to about 5 wt. % of the one or more fluorocarbon elastomer compatibility improving agents, based on the total weight of the lubricating oil composition.

10. The method of claim 1, wherein the lubricating oil composition further comprises one or more lubricating oil additives selected from the group consisting of an antioxidant, detergent, rust inhibitor, dehazing agent, demulsifying agent, metal deactivating agent, friction modifier, antiwear agent, pour point depressant, antifoaming agent, co-solvent, package compatibiliser, corrosion-inhibitor, dye, extreme pressure agent, and mixtures thereof.

11. The method of claim 1, wherein the one or more oil-soluble titanium compounds are represented by the general formula:

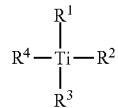

wherein $R^1$, $R^2$, $R^3$ and $R^4$ are independently a hydrocarbyloxy-containing group.

12. The method of claim 11, wherein each $R^1$, $R^2$, $R^3$ and $R^4$ is independently a $C_1$ to $C_{20}$ alkoxy group.

13. The method of claim 11, wherein at least two of $R^1$, $R^2$, $R^3$ and $R^4$ of the oil-soluble titanium compound are the same $C_1$ to $C_{20}$ alkoxy group.

14. The method of claim 11, wherein at least three of $R^1$, $R^2$, $R^3$ and $R^4$ of the oil-soluble titanium compound are the same $C_1$ to $C_{10}$ alkoxy group.

15. The method of claim 11, wherein each of $R^1$, $R^2$, $R^3$ and $R^4$ of the oil-soluble titanium compound is the same $C_1$ to $C_{20}$ alkoxy group.

* * * * *